United States Patent [19]

Dankó et al.

[11] Patent Number: 4,933,887
[45] Date of Patent: Jun. 12, 1990

[54] PROCESS AND APPARATUS FOR THE DETERMINATION OF THERMO-PHYSICAL PROPERTIES

[75] Inventors: György Dankó; István Czifka, both of Budapest, Hungary

[73] Assignee: Budapesti Muszaki Egyetem, Hungary

[21] Appl. No.: 296,310

[22] Filed: Jan. 6, 1989

Related U.S. Application Data

[63] Continuation of Ser. No. 862,029, May 12, 1986, abandoned.

[30] Foreign Application Priority Data

May 10, 1985 [HU] Hungary .................... 1764/85

[51] Int. Cl.$^5$ .................... G01N 25/72; G01N 25/18
[52] U.S. Cl. ........................... 364/557; 374/5; 374/44; 374/136
[58] Field of Search ............... 364/550, 551.01, 557; 374/5, 7, 43, 44, 136

[56] References Cited

U.S. PATENT DOCUMENTS

| | | | |
|---|---|---|---|
| 2,587,705 | 3/1952 | De Forest | 374/5 |
| 3,016,732 | 1/1962 | Hanysz et al. | 374/7 |
| 3,217,550 | 11/1965 | Birman | 374/136 |
| 3,222,917 | 12/1965 | Roth | 374/5 |
| 3,555,879 | 1/1971 | Schroeer et al. | 374/5 |
| 3,938,383 | 2/1976 | Sayer | 374/44 X |
| 4,469,451 | 9/1984 | Kunetka et al. | 374/136 |
| 4,476,716 | 10/1984 | Fons | 374/136 X |
| 4,575,261 | 3/1986 | Berger et al. | 374/136 |
| 4,616,705 | 10/1986 | Stegemeier et al. | 374/136 X |

FOREIGN PATENT DOCUMENTS

| | | | |
|---|---|---|---|
| 0135767 | 5/1979 | Fed. Rep. of Germany | 374/43 |
| 0163856 | 10/1982 | Japan | 374/43 |
| 0911278 | 3/1982 | U.S.S.R. | 374/44 |
| 1602255 | 5/1978 | United Kingdom | |
| 2177201 | 1/1987 | United Kingdom | 374/44 |

OTHER PUBLICATIONS

Moore, J. P. et al, "Precision measurements of the thermal conductivity, electrical resistivity and Seebeck coeff. from 80 to 400 K and their application to pure molybdenum", *Review of Scientific Instruments*, vol. 45, No. 1, Jan. 1974, pp. 87–95.

Bondi, P. et al., "Rapid Method for the Measurement of the Thermal Diffusivity of Rocks", Conference: Advances in Thermal Conductivity, Lake Ozark, Mo., U.S.A., Nov. 5–7, 1974, pp. 389–397.

Donaldson; A. B., "Thermal diffusivity measurement by a radial heat flow", *Journal of Applied Physics*, vol. 46, No. 10, pp. 4584–4589, Oct. 1975.

*Primary Examiner*—Parshotam S. Lall
*Assistant Examiner*—Joseph L. Dixon
*Attorney, Agent, or Firm*—Handal & Morofsky

[57] ABSTRACT

A process for the simultaneous, in-situ determination of thermophysical properties, primarily for determination of the thermal conductivity and thermal diffusivity, according to which in a certain volume of the material to be tested a temperature field varying with time is brought about by perturbation due to heating and this temperature field is measured, then certain properties are determined by calculation from the obtained temperature data and the known heating power input spherical isotherms are formed in the material to be tested in a way, that temperature change of at least one degree Celsius is brought about at the measuring points which are arranged along a straight line passing through the heat source and intersecting the isotherms along their diameter, and a measuring probe formed as a rod-type body made of poor heat conductive material having a heating element and measuring points, wherein the heating element is formed as a point-like heat source.

20 Claims, 4 Drawing Sheets

PROCESS AND APPARATUS FOR THE DETERMINATION OF THERMO-PHYSICAL PROPERTIES

This application is a continuation of application Ser. No. 862,069, filed May 12, 1986 now abandoned.

FIELD AND BACKGROUND OF THE INVENTION

The present invention relates to the simultaneous, in-situ determination of thermophysical properties, particularly of heat conductivity and thermal diffusivity, in the course of which a perturbated temperature field varying with time is produced in a certain volume of the material to be tested by heating, this temperature field is measured, then the required properties are determined by calculation from the obtained temperature data and heating power, as well as it relates to a measuring probe for the implementation of above process.

The importance of measuring heat conductivity and thermal diffusivity needs no verification. It is also known that in the case of inhomogeneous materials such as granulites, heaps of seeds, the earth's crust, or stratified rock mantle around an underground airway, the equivalent, averaged thermophysical properties can be measured most reliably in-situ, because they may be dependent on the concrete occurrences, pressures, moreover on the local moisture content. With sampling and laboratory measuring, systematic differences in the values to be determined may occur as compared to the in-situ state. All these emphasize the importance of the in-situ measurement in each case when a material of non-standard quality is in question. However, in the in-situ measurement technique only various attempts can still be observed. The same can be detected in the field of measurement technique applied to mine rocks: several ingenious ad-hoc methods are used for measuring the thermophysical properties of the rock mantle of airways in mines which can be summed up as follows:

One of the groups of the in-situ methods is represented by the short-probe transient heat conductivity measurements. This kind of measurement is performed by means of a probe equipped with linear heat source in its centerline. Thermocouples are arranged on the surface of the probe. The heat conductivity of the rock can be determined from the temperature rise measured within a time interval subsequent to switching on the heat source. Such solution is described in the UK Patent 2 071 319.

The drawback of the mentioned methods is that cylinder-symmetrical isotherms are assumed around the probe in the course of evaluation, but this symmetry is not necessarily true and it can be checked by measurement, since only the surface temperature of the probe can be measured instead of the full temperature field. The probe, however, is heated, hence the temperature difference between that of the probe surface and the rock should be reduced by careful probe installment but its complete elimination is not possible. These methods are applicable only to the determination of heat conductivity.

The second group of the in-situ measurement include the methods based on measuring and evaluation of transient cylinder symmetrical temperature distribution. This group of measurement is used for example in mines, when the temperature field around the mine airway is measured, as varying with the ventilation time, while the temperature distribution is measured in the radial bore holes characteristically 5 to 30 m deep (Hitchcock-Jones . . . Heat flow into a new main roadway Colliery Engineering, Feb.-Mar. 1985pp. 73-76 and 117-122, as well as Jones: Air temperature along a main intake roadway, Colliery Guardian, Jun. 1964, pp. 844-850). In this case it is assumed that the temperature of the ventilating air is constant during the whole time period of the measurement and a step-wise change in the air temperature was brought about at the very beginning of the measurement. This undoubtely involves inaccuracies, since the measurement takes long enough time, generally several months. Ventilating air of varying temperature was assumed in other measurement methods and the evaluation was performed accordingly. Temperature changes with time recorded in at least two different depths of the rock wall are needed for the evaluation. (Cifka-Danko-Eszto: In-situ determination of the thermal diffusivity of rocks around underground airways. Publication of the Hungarian Central Institute for the Development of Mining, 1979, No. 22, pp. 133-138). On the other hand, others may use three or more different depths. (For example Vost, K. R.: "In-situ measurements of Thermal Diffusivity of Rock Around Underground Airways", Transaction of I.M.M., Vol. 85, pp. A57-A62.)

Measurements using fast heating of the rock surface are listed in the third group. Perturbations planned and performed carefully are applied to changing the temperature field. Consequently, the boundary conditions are known and a simple and accurate evaluation can be attained. For example, the fast heating of a closed roadway section was used and the temperature change with time of the rock was measured relatively close to the surface in the hole drilled into the rock surface. (Sherratt-Hinsley: A heating experiment to determine the thermal constants of rocks in-situ, The Mining Engineer, 1961, No. 3871, pp. 700-711). The method is suitable for the determination of both properties, i.e. heat conductivity and thermal diffusivity.

Experiments were conducted also by means of more indirect methods of in-situ measurement, for example the thermophysical properties are determined from the temperature rise of the air flowing along a roadway section of given length.

Such special measurements were also performed when in the bore hole drilled in the rock, the originally longitudinal temperature gradient is practically shunted with a probe of good thermal conductivity and the change of the temperature gradient is measured (U.S. Pat. No. 3 808 889).

OBJECTS AND SUMMARY OF THE INVENTION

The object of the present invention is to eliminate the described shortcomings and to provide a process and device, whereby the various thermophysical properties, primarily the heat conductivity and thermal diffusivity can be determined independently from each other within a single measuring period in a way that the inaccuracies arising from model errors during the evaluation remain on a minimum level and, for the sake of satisfactory measurability, measurement based on active thermal perturbation is performed.

According to this invention, a point-like heat source is applied as a heater for the temperature field perturbation in the process of determining thermophysical properties, whereby spherical isotherms are generated in the material to be tested, so that a temperature change of at least one degree Celsius is brought about in the measuring points, which are arranged along a straight line passing through the heat source and intersecting the spherical isotherms along their diameter.

Heating is generally carried out with constant heat flux density, and the temperature measurements are performed in at least three measuring points, at least at two consecutive points of time and for maximum ten hours. The measurements may take place on one or both sides of the heat source. The temperature of the extreme isotherm outside the perturbated temperature field is constantly checked during measurement, so that slow thermal disturbances coming from the surrounding area could be detected and taken into account in the evaluation process.

The probe used for the implementation of the above process is designed in the form of a rod-shaped body containing a heating element and temperature measuring points (sensors) in longitudinal direction, while the probe sections between the measuring points or the measuring points and the heating element are, made of a material having a poor heat conductivity and according to the invention, the heating element is formed as a point-like heat source.

In this description, the point-like heat source i.e. the heating element is considered as a part of the probe whose maximum size, generally its length is shorter at least by one order of magnitude than the distance between the farthest active measuring point and the heating element.

Active measuring points are considered in this description which are situated within the perturbated temperature field produced by heating. Those outside this field are considered as passive measuring points, one of them is the reference point of the measuring points, which is farthest from heating element.

The heating element is mounted on or in an elastic ring made suitably of good heat conductive material and the measuring points may be on one or both sides of the heating element. The measuring points are formed suitably as surface temperature sensors, preferably thermocouples. A measuring point formed as reference point can be at one end of the probe simultaneously serving, as the cold junction of the thermocouples. Suitably, at least a fraction of the measuring points is formed as series connected thermocouples.

The probe is equipped suitably with control and evaluating systems some parts of which can be implemented by a computer.

The process and apparatus specified in the present disclosure are used for measuring heat conductivity ($\lambda$) and/or thermal diffusivity (a) of solid state, or other completely stationary materials. No sample of the material to be tested is required for the measurement, but drilling of a test hole is sufficient. This makes the method particularly suitable for in-situ measurements. The volume of material needed for the measurement can be chosen within broad limits by the parameters of the procedure, among them by the time period of the measurement. In this way, it can be ensured that in case of inhomogenities in the material tested, the measured parameter refers to the average of a larger mass, incidentally of several hundred kg. The time required for measurement is usually less than 8 hours.

The probe is a 1 to 2 m long rod of a few cm in diameter fitting into the test hole. The central unit of the measuring system may be a fully automatic electronic instrument, which performs the temperature field perturbation and the measurements in space and time. Measurement of temperature changes brought about by the heating intervention takes place in several points and several times during the measuring period. The unknown thermophysical properties i.e. "$\lambda$" and "a" then are calculated using the measured data of the temperature field and the governing equations of the transient heat conduction.

The fundamental idea of this measuring method according to the invention is that transient temperature distribution characterized by spherical isotherms is brought about in the tested material as a thermal perturbation, generated by an approximately point-type heat input, the isotherms are measured in several points along a radius (or diameter) at sufficiently frequent intervals during the test-period. In the course of evaluation thermal diffusivity is determined by means of a finite difference scheme matched to two consecutive temperatures in time of three adjacent spherical surfaces. This finite difference scheme is derived from the Fourier differential equation of heat conduction while the heat conductivity is calculated from the temperature of a single spherical surface varying with time, and on the basis of the knowledge of the perturbating heat source i.e. the heat flux density coming from the point-like heating element.

BRIEF DESCRIPTION OF THE DRAWINGS

Further details of the invention are described by way of example with the aid of drawings, in which.

DESCRIPTION OF THE PREFERRED METHOD AND EMBODIMENTS

Figure 1:
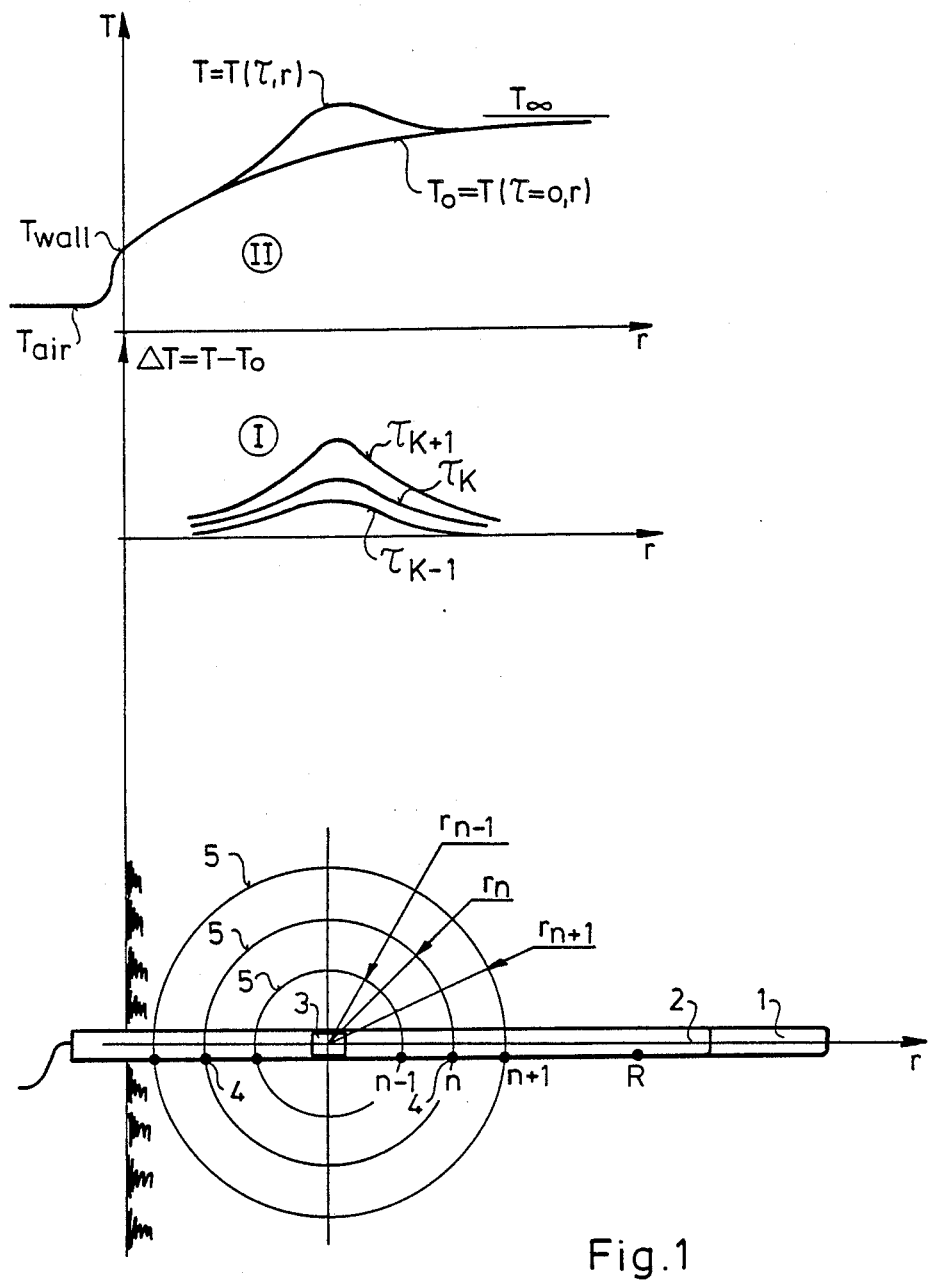
FIG. 1: Outline of probe and measurement according to the invention

FIG. 1 shows the outline of the measurement according to the invention. Probe 2 fitted into bore hole 1 is equipped with a heating element 3, to produce temperature differences. Cables are attached to the free end of the probe 2. These supply the energy required for heating and connect the probe 2 with the measuring units.

Measuring points are formed on both sides of the heating element 3. The isotherms 5 developing during heating are measured at these measuring points. One of the extreme measuring points is formed as reference point R. This measuring point should always be situated outside the temperature field perturbed by heating.

Heating element 3 is positioned in the origin of a co-ordinate system, where the measuring points 4 are arranged along different radii r. in relation to heating element 3.

FIG. 1 shows the curves of the temperature change brought about by heating. These are shown in diagram I at different points of time $\tau$. In fact these curves are superposed on the temperature distribution existing originally in the material, as shown in diagram II. Therefore, the measurement of the initial, unperturbed temperature distribution is also needed, and this initial distribution is always to be subtracted from the distributions obtained during the measurement. The initial distribution is regarded as constant for the duration of the measurement, what is generally permissible on account of the short length of time, but the condition should be examined and the testing depth is to be determined with regard to this. A cooling process, too, can be used by way of checking for the determination of thermal diffusivity "a".

The measuring apparatus required for the measuring process consists of probe 2 and the instruments for measurement, control and evaluation.

In a preferred embodiment of the invention, heating element 3 used in probe 2, contrary to the known solutions in the literature, is formed not as a linear but as a point-type heat source. Accordingly, the isothermic surfaces in the medium (in case of homogeneous testing material) will take a spherical shape instead of cylindrical surfaces.

For the determination of thermal diffusivity "a" the temperature changes with time observed at different measuring points 4 should be used. Evaluation of the measurement is based on matching the measured temperature change to the calculated values using the describing differential equation. With the use of three adjacent measuring points e.g. points $n-1$, $n$ and $n+1$ corresponding to points $r_{n-1}$, $r_n$ and $r_{n+1}$, as well as with the use of two consecutive points of time, e.g. points of time $\tau_k$ and $\tau_{k+1}$ shown in diagram I, the solution of the differential equation derived from the Fourier diffential equation does not require the application of separate boundary condition equation, or more exactly boundary condition of the first kind is used implicitly. Parameter "a" offering the best fitting can be considered as the final result of the measurement evaluation. The knowledge of the perturbating heat flux input is not required for the evaluation, hence the determination of "a" and $\lambda$ is independent from each other.

Heating perturbation of such intensity is required for the measurement, which generates a well measurable, e.g. 10° C. temperature change within a few hours at the point of heating. Recording the temperature rise with time brought about by heating is required in several, but at least three times during measurement. Then the unknown properties should be determined by calculation from the temperature changes with time on the basis of the mathematical model of the temperature change brought about by the perturbation.

Figure 2:
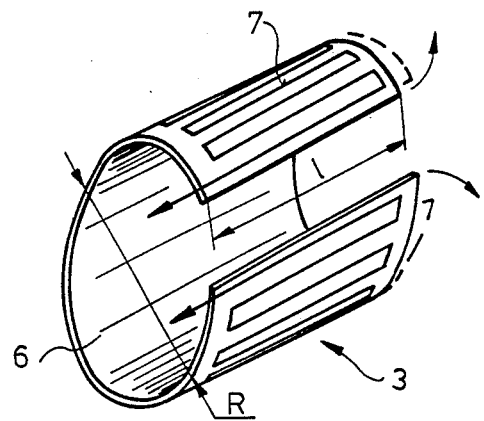
FIG. 2: Design of the heating element

Heating element 3 which can be found about the centre of the probe, is an electric surface heating layer the length of which is approximately equal to its diameter whose own thermal capacity is low. For the sake of good contact with the surface of the tested material, the heating layer is formed as filament 7 mounted on elastic ring 6 as shown in FIG. 2. The elasticity of elastic ring 6 is ensured by a longitudinal slit.

The temperature sensors for measuring the spherical isotherms are spaced along the length of the probe. The measuring points 4 should be arranged at least in one direction moving away from the point-like source and with a view to simple evaluating calculation, in a uniform spacing. The sensors can be arranged also in both directions moving away from the point-like heat source and this allows of checking the spherical symmetry of the isotherms at least along one diameter. In the case of differences, the calculation can be corrected by averaging or by other ways. The surface temperature sensors should be fastened onto the surface similarly to fastening the heating layer. In the case of using elastic rings, the rings should be contracted when the sensors are inserted to prevent damage. Thermocouples can be used as temperature sensors, which are particularly suitable for measuring temperature differences. The difference formation is rendered possible by arranging the reference point R, i.e. the cold junction of the thermocouples in a point sufficiently far from the place of the heat source (such as 1 m), as undisturbed by the heater during measurement. It is possible to use several series connected thermocouples in each measuring point, the hot junctions of which are arranged in the respective measuring points, and the cold junctions in the reference point. In this way the measuring signal and the accuracy can be increased. The number of series connected thermocouples may vary at each measuring point and can be increased when moving away from the point-like heat source whereby relatively more intensive measuring signal can be obtained at the points where the temperature change is lower, and thus the accuracy can be increased.

A multi-channel, measuring data acquisition instrument or system of general purpose can be used for measuring, recording and evaluating the signals of the temperature sensors. In the course of measurement heating should be switched on (or switched off for the control measurement during cooling down), and for this purpose a supplementary heating unit is necessary which is synchronized with the measuring unit, i.e. controlled by the control unit. The block diagram of such instrument supplemented with heating unit is shown by way of example in FIG. 3.

Figure 3:
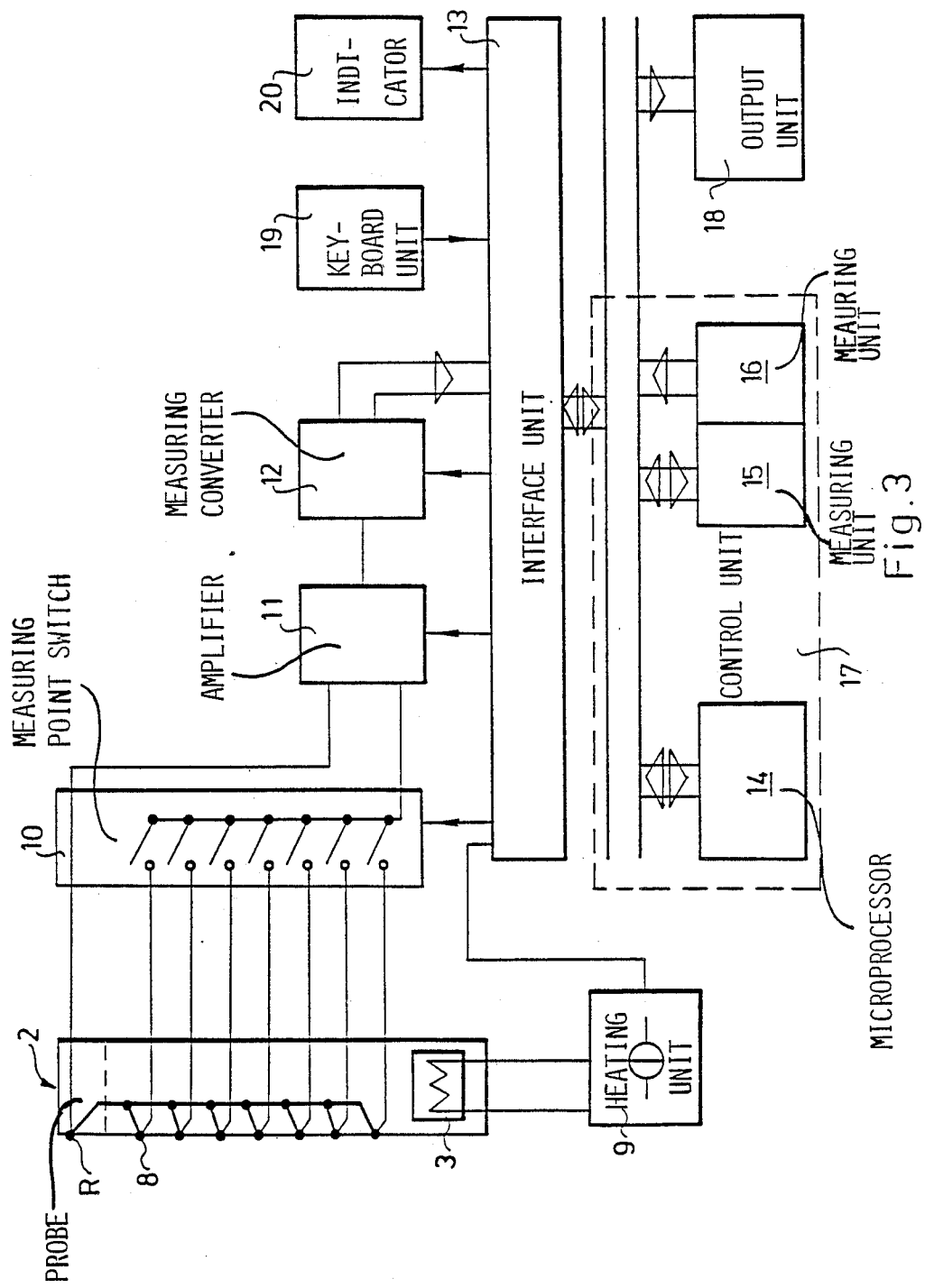
FIG. 3: Connection layout of elements of the probe

The probe 2 according to the invention with the heating element 3 and thermocouples 8 forming the measuring points are shown on the left side of FIG. 3. Heating element 3 is connected with the heating unit 9 controlling the active thermal intervention. Thermocouples 8 are connected to the measuring point switch 10 with the help of which the temperature sensing thermocouple can be selected.

The microvolt size thermovoltages obtained during the measurement are amplified by $10^3$-$10^4$ order of magnitude with the help of amplifier 11. Measuring converter 12 is connected to amplifier 11, which is an analog-digital measuring converter and forms the numerical values of the measured voltage.

An interface unit 13 ensures the connection between the peripheries and the central unit. A control unit 17 formed by measuring units 15 and 16 as well as a microprocessor 14 is connected to the interface unit 13. The memory areas RAM and ROM of measuring units 15 and 16 are suitable for the storage of measuring data, as well as the measuring control and evaluating computational programs.

Output unit 18 can be connected to the control unit 17. Control unit 17 can be the central unit of a computer.

The instrument also includes a keyboard unit 19 and an indicator 20 for the display of the final results.

A measuring process is introduced by way of example as follows:

Measurements were performed in the andesitic rock of a mine. About 1 m deep hole was drilled into this rock for the probe of the measuring system.

The surface heat flux density ensured by the heating element used in the probe was $q = 10^4$ W/m$^2$, the radius of the heating element formed as point-type heat source was $R = 0.02225$ m, the length $l = 0.05$ m.

The measuring points are spaced along the probe as follows:

r(m) = 0.0225; 0.1; 0.125; 0.15; 0.175 0.2; 0.225; 0.25; 0.275; 0.3 0.325; 0.35; 0.375; 0.4; 0.425 0.45; 0.475; 0.5; 0.525; 1.0.

The measurements were performed at the following time intervals: $\tau(s) = $ 226; 450; 900; 1800; 3600; 5400; 7200; 9000; 10 800; 12 600; 14 400; 16 200; 18 000; 19 800; 21 600; 23 400; 25 200; 27 000; 28 800.

The set of curves shown in diagram I are obtained during the measurement. According to the given measurement results it is evident that at the point of time of the last measurement i.e. at the 8.5th hour, the radius of the penetration depth, i.e. the perturbed area is about 1 m. Hence it follow that the reference point should be arranged beyond this distance.

The temperatures of the curves belonging to the first few points of evaluation since the perturbation has not enough penetration depth, hence it is advisable to start the evaluation in the 2nd hour.

The value of the max. temperature rise in the first measuring point on radius r = 0.0225 m was 80.9° Kelvin at the last measuring point of time.

Figure 4:
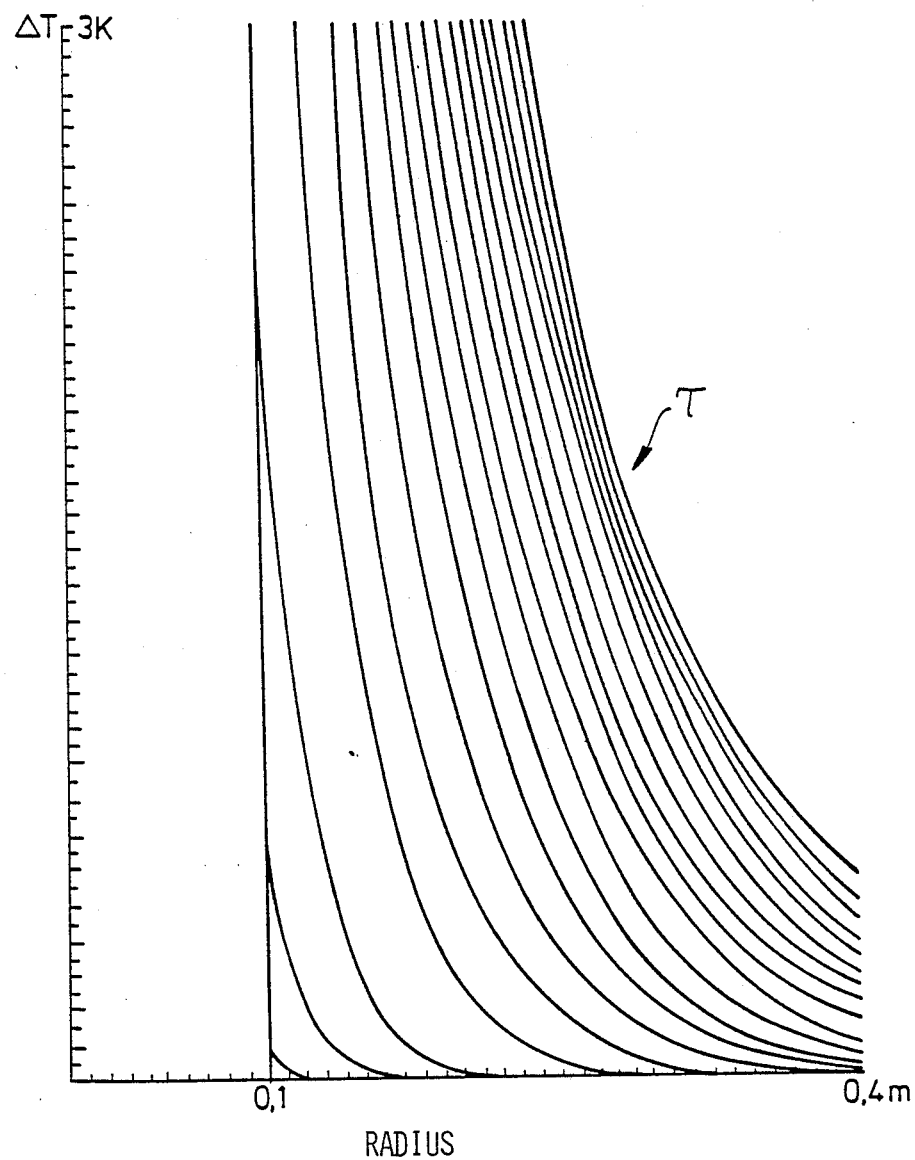
FIG. 4: Temperature field obtained during the measurement process according to the invention.

It is advisable to perform the evaluation in the middle part of the temperature field. This is shown in FIG. 4, which is the set of curves matched to the measured temperature distribution.

Between temperatures $T_{n-1,k}$, $T_{n,k}$ and $T_{n+1,k}$ obtained at three adjacent radii at the same time $T_k$ and the temperature $T_{n,k+1}$ related to the next point of time at the middle position, the following difference equation can be derived from the descriptive Fourier differential equation of heat conduction:

$$T(n, k+1) = \frac{2 a \Delta\tau}{r^2} \left( \frac{T_{n+1,k} \cdot r_{n+1} + T_{n-1,k} r_{n-1}}{2} \right) - T_{n,k}\left( \frac{2a \Delta\tau}{r^2} - 1 \right) \quad (5)$$

From above equation it follows that the thermal diffusivity "a" can be calculated from four different temperature values ($T_{n,k+1}$; $_{n+1,k}$; $T_{n-1,k}$ and $T_{n,k}$). Its value from the measurement was given as a = $10^6$ m²/s.

Since the temperature field of spherical isotherms function r and $\tau$ is known in the following form $$T(r,\tau) = \frac{q \cdot R^2}{\lambda \cdot r} \cdot f(r,\tau)$$

thermal conductivity $\lambda$ with the knowledge of "a" and heat flux density "q" can be recalculated from a single measured temperature. In this case, the value of the thermal conductivity was $\lambda$ = 2.5 W/mK.

It was shown that the calculation formulae of the temperature distribution could be used in reverse order during evaluation to calculate the unknown thermophysical properties. However, it is advisable to perform several evaluations then averaging; method of the least squares fit can be used during this work.

The examples demonstrate that the process according to the invention, in the course of which point like heat source is used and accordingly, spherical isotherms are obtained in the medium, is suitable for the determination of different thermophysical properties, C.e. for determination of heat conductivity and thermal diffusivity independently from each other within a single measuring period. The measurement is extremely simple, but it needs a sophysticated measuring apparatus. The inaccuracies due to model-error occuring during evaluation can be kept at a low level. Consequently, the process and the probe can be used well for in-situ measurings.

We claim:

1. A process for the in situ determination of thermophysical properties of a solid material, primarily for determination of thermal conductivity and thermal diffusivity in a certain volume of a solid, stationary material to be tested, comprising the steps of making a hole in said material, inserting into said hole in said solid stationary material a probe having a number of temperature sensors and a heat source, generating a temperature field varying with time with said heat source by way of driving with a known heating power input, measuring the temperature field at a plurality of measuring points on the inside surface of said hole in the material to generate temperature data for said plurality of measuring points, said sensor being in intimate contact with said material at said measuring points whereby the space for convection currents in said hole is minimized and measurement may be taken substantially without the interference of convection currents, determining selected properties by calculation from said temperature data and the known heating power input, wherein said pointlike heat source is used in contact with said material for heating to form substantially spherical isotherms in a perturbed portion of the material to be tested to induce a measurable temperature change at the measuring points, said measuring points at different distances from the heat source being arranged along a straight line passing through the heat source and intersecting the isotherms along their diameter, wherein the measuring points are selected so that the maximum size of the point-like heating element is substantially smaller than the distance between the point-like heating element and the farthest measuring point.

2. A process as in claim 1, wherein a constant heat flow density is used for generating said spherical isotherms.

3. A process as in claim 1, wherein the measurements are performed at least at two consecutive points of time.

4. A process as claimed in claim 1, wherein measurements are performed at three or more measuring points.

5. A process as claimed in claim 1, wherein measurements are performed for a maximum of 10 hours.

6. A process as claimed in claim 1, wherein the measurements are performed at points substantially in a line which extends from the point-like heat source along the length of said hole to the entry point of said hole into said material.

7. A process as claimed in claim 1, wherein measurements are performed at points disposed in a line along the length of said hole, the point-like heat source being positioned between each of said opposite hole ends and measurement being performed at points between said source and one of said ends of said hole and at points between said source and the other of said ends of said hole.

8. A process as in claim 7, wherein said points are disposed at symmetrical positions with respect to said point-like heat source and wherein the temperature of a reference point is measured, said point being outside the perturbated temperature field.

9. A measuring probe for the simultaneous in situ determination of thermophysical properties, primarily for determination of the thermal conductivity and thermal diffusivity in a large volume of a solid stationary material, comprising a rod-like body made of poorly heat conductive material, a heating element formed as a point-like heat source to form substantially spherical isotherms, and a plurality of measurement elements, substantially for measuring a thermal characteristic of said solid stationary material, disposed at points along the length of said rod-like body, the maximum size of said heating element being substantially smaller than the distance between the heating element and the farthest measurement element, said rod-like body together with said heat source and said measurement elements being configured for insertion into intimate continuous physical contact with a sidewall of a borewall in said solid stationary material.

10. A probe as claimed in claim 9, wherein the heating element is mounted with an expandable elastic ring made of highly heat conductive material producing a sealing engagement with said borehole wall preventing convective currents in said borehole.

11. A probe as in claim 9, wherein the measuring points are arranged in a line which extends from said heat source along the length of said hole to the entry point of said hole into said material.

12. A probe as in claim 9, wherein a reference element is positioned at one end of the probe.

13. A probe as in claim 12, wherein the measurement elements are surface temperature sensors.

14. A probe as in claim 13, wherein the surface temperature sensors are thermocouples.

15. A probe as in claim 14, wherein the reference element is a cold junction of said thermocouples.

16. A probe as in claim 14, wherein at least a portion of said measurement elements are connected in series.

17. A probe as in claim 9, further comprising means to control said measurement elements, said reference element and said point-like source.

18. A probe as in claim 9, further comprising means to evaluate the output of said measurement elements and said reference element.

19. A measuring probe for the simultaneous in-situ determination of thermophysical properties, primarily for determination of the thermal conductivity and thermal diffusivity in a large volume of a solid stationary material, comprising a rod-like body made of poorly heat conductive material, a heating element formed as a point-like heat source for generating substantially spherical isotherms in said solid stationary material, and a plurality of measurement elements, substantially for measuring a thermal characteristic, disposed at points along the length of said rod-like body, the maximum size of said heating element being smaller at least by one order of magnitude, than the distance between the heating element and the farthest measurement element, said rod-like body together with said heat source and said measurement elements being configured for insertion into thermal and physical contact with a sidewall of a borehole, said measuring points being arranged on opposite sides of said heating element and wherein a reference element is positioned at one end of the probe.

20. A probe as in claim 19, wherein said measurement elements occur in pairs at opposite sides of said heating element and each element of each pair is arranged equidistant from the heat source.

* * * * *